(12) United States Patent
Bazan et al.

(10) Patent No.: US 7,094,929 B2
(45) Date of Patent: Aug. 22, 2006

(54) WATER-SOLUBLE DISTYRYLBENZENE CHROMOPHORES FOR APPLICATIONS IN OPTOELECTRONIC TECHNOLOGIES

(75) Inventors: Guillermo C. Bazan, Santa Barbara, CA (US); Bernhard Koehler, Seligenstadt (DE); Alexander Mikhailovsky, Ventura, CA (US); Hadjar Benmansour, Goleta, CA (US); Bin Liu, Singapore (SG); Janice W. Hong, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 116 days.

(21) Appl. No.: 10/801,963

(22) Filed: Mar. 15, 2004

(65) Prior Publication Data

US 2004/0192968 A1 Sep. 30, 2004

Related U.S. Application Data

(60) Provisional application No. 60/456,289, filed on Mar. 20, 2003, provisional application No. 60/454,840, filed on Mar. 14, 2003.

(51) Int. Cl.
*C07C 211/50* (2006.01)
*C07C 211/63* (2006.01)

(52) U.S. Cl. .............. 564/290; 564/286; 564/289
(58) Field of Classification Search ............. 564/286, 564/289, 290
See application file for complete search history.

(56) References Cited

U.S. PATENT DOCUMENTS

| | | | | |
|---|---|---|---|---|
| 4,009,193 | A * | 2/1977 | Scheuermann et al. | 558/27 |
| 4,314,820 | A * | 2/1982 | Weber et al. | 8/648 |
| 4,339,393 | A * | 7/1982 | Luthi et al. | 558/27 |
| 6,022,998 | A * | 2/2000 | Kawaguchi et al. | 564/434 |
| 6,267,913 | B1 * | 7/2001 | Marder et al. | 252/582 |
| 6,608,228 | B1 * | 8/2003 | Cumpston et al. | 564/308 |

* cited by examiner

*Primary Examiner*—Brian Davis
(74) *Attorney, Agent, or Firm*—Berliner & Associates

(57) ABSTRACT

Two-photon or multi-photon chromophores having a conjugated pi-electron system with donating groups at each end of the pi-electron system providing charge-transfer properties, and having quaternary amine groups that can enhance the solubility of the chromophore in water. In a particular embodiment, the chromophore is based on a distyrylbenzene core, with donor or acceptor groups attached to the central benzene ring.

16 Claims, 2 Drawing Sheets

WATER-SOLUBLE DISTYRYLBENZENE CHROMOPHORES FOR APPLICATIONS IN OPTOELECTRONIC TECHNOLOGIES

CROSS-REFERENCE TO RELATED APPLICATIONS

This application claims the benefit of U.S. Provisional Application No. 60/454,840, filed on Mar. 14, 2003, and U.S. Provisional Application No. 60/456,289, filed on Mar. 20, 2003.

BACKGROUND

1. Field of Invention

This invention relates generally to chromophores having two-photon or multi-photon absorptivity.

2. Related Art

Organic molecules that absorb two or more photons simultaneously have wide application in a variety of technologies involving such subjects as thin film transistors, light emitting diodes, optical data storage, 3-D microfabrication techniques, host structures providing polar environments and precluding fluorescence quenching, and initiators of polymerization reactions. Two features of the two-photon absorption process make these applications feasible. The first is the quadratic dependence of two-photon absorption on the intensity of the incident radiation. This allows for three dimensional spatial resolution. The second feature is the absence of single-photon absorption, which allows an incident light beam to penetrate deeper into a material than would be possible with single-photon approaches.

Two photon or multi-photon absorbing molecules have been designed based on conjugated pi-electron systems with donating groups at each end of the pi-electron system providing charge-transfer properties. For example, U.S. Pat. Nos. 6,267,913 and 6,608,228, both incorporated by reference herein, describe two photon absorption chromophores having electron donors such as amino or alkoxy groups attached to a bridge of pi-conjugated bonds. The absorption of two or more photons by such molecules can trigger chemical and physical changes that make these molecules useful for two-photon applications. Although much progress has been made in developing two-photon or multi-photon molecules, additional two-photon or multi-photon absorbing materials, especially water-soluble materials, are needed to fully exploit two-photon applications.

SUMMARY

The present invention is directed to a new class of organic chromophores having a conjugated pi-electron system with donating groups at each end of the pi-electron system providing charge-transfer properties. The donating groups have quaternary amine moieties that can enhance the solubility of the chromophores in water.

More particularly, the present invention is directed to chromophores having the general formula (I):

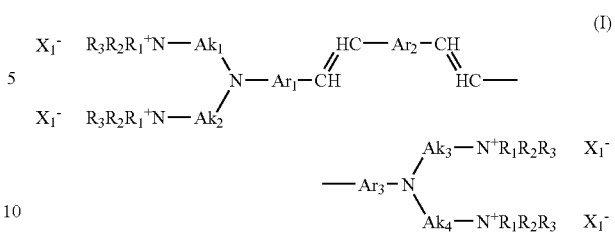

wherein $Ar_1$, $Ar_2$ and $Ar_3$ are each independently a substituted or non-substituted aromatic hydrocarbon or aromatic heterocyclic ring; $Ak_1$, $Ak_2$, $Ak_3$ and $Ak_4$ are each independently a substituted or non-substituted alkyl or alkylene group; $R_1$, $R_2$ and $R_3$ are each independently a substituted or non-substituted alkyl group; and $X_1$ is a counter anion.

DETAILED DESCRIPTION OF THE INVENTION

Figure 1:
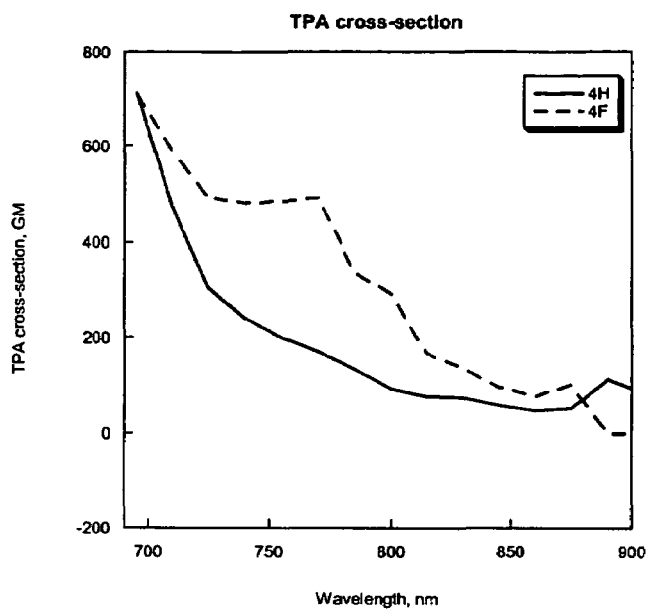
FIG. 1 is a graph showing the two-photon absorption of a molecule of this invention.

In the chromophore of formula (I), $Ar_1$, $Ar_2$ and $Ar_3$ are each independently a substituted or non-substituted aromatic hydrocarbon, or a substituted or non-substituted aromatic heterocyclic ring. As used herein, an aromatic hydrocarbon is a carbocyclic group that contains a (4n+2) pi-electron system, where n is an integer. Aromatic hydrocarbons can include such hydrocarbons as benzene, naphthalene and toluene.

As used herein, an aromatic heterocyclic ring is a cyclic group of atoms that contains a (4n+2) pi-electron system, with at least one atom within the ring being an element other than carbon. Aromatic heterocyclic rings can include groups having a non-carbon ring element of oxygen, sulfur or nitrogen, such as thiophene, furan, pyran, chromene, and pyridine.

Preferably, $Ar_1$, $Ar_2$ and $Ar_3$ are single ring aromatic hydrocarbons. More preferably, $Ar_1$, $Ar_2$ and $Ar_3$ are benzene rings.

Each of $Ar_1$, $Ar_2$ and $Ar_3$ can independently have one or more substituent groups, with two being preferable and one being most preferable. Substituent groups can include such groups as:

a) linear or branched alkyl groups of up to 25 carbon atoms such as methyl, ethyl, propyl, butyl, sec-butyl, tert-butyl, pentyl, hexyl, heptyl, octyl, stearyl, 1-methylpentyl, 5-methylhexyl, and 2-phenylisopropyl;

b) $(CH_2CH_2O)_\alpha$—$(CH_2)_\beta CO_2R_{a1}$—$(CH_2CH_2O)_\alpha$—$(CH_2)_\beta OR_{a2}$; —$(CH_2CH_2O)_\alpha$—$(CH_2)_\beta NR_{a3}R_{a4}$; —$(CH_2CH_2O)_\alpha$—$(CH_2)_\beta CONR_{a3}R_{a4}$; —$(CH_2CH_2O)_\alpha$—$(CH_2)_\beta CN$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$; —$(CH_2CH_2O)_\alpha$—$(CH_2)_\beta$—Phenyl; where $R_{a1}$, $R_{a2}$, $R_{a3}$, and $R_{a4}$ are each independently H, or a linear or branched alkyl group with up to 25 carbon atoms, and $\alpha$ is 0–10 and $\beta$ is 1–25;

c) aryl groups such as aromatic hydrocarbons containing up to 20 carbon atoms including phenyl, naphthyl, furanyl, thiophenyl, pyrrolyl, selenophenyl and tellurophenyl;

d) fused aromatic rings such as naphthalene and anthracene;

e) $NR_\alpha R_\beta$; $OR_\gamma$; CHO; CN; $NO_2$; Br; Cl; I; phenyl; where $R_\alpha$, $R_\beta$ and $R_\gamma$ are each independently H or compounds such as those in a), b), c) and d) above; and f) a donor or acceptor group.

The term "donor" refers to an atom, or group of atoms, with a low ionization potential that can be bonded to a π (pi)-conjugated bridge. Exemplary donors are: I, Br, Cl, OC(O)R", SH, OH, SR", OR", NHC(O)R", $NH_2$, NH"R, $S^-$, and $O_-$, where R" refers to an alkyl group containing 1–50 carbon atoms. A preferred donor is $OCH_3$.

The term "acceptor" refers to an atom, or group of atoms, with a high electron affinity that can be bonded to a π (pi)-conjugated bridge. Exemplary acceptors are: F, C(O)NR"$_2$, C(O)NHR", C(O)NH$_2$, C(O)OR", C(O)OH, C(O)R", C(O)H, CN, S(O$_2$)R", and NO$_2$, where R" refers to an alkyl group containing 1–50 carbon atoms. Preferred acceptors are F and CN.

In the foregoing, the term "bridge" refers to a molecular fragment that connects two or more chemical groups.

In the chromophore of forumla (I), $Ak_1$, $Ak_2$, $Ak_3$ and $Ak_4$ are each independently a substituted or non-substituted alkyl or alkylene group. The alkyl or alkylene group can be a linear or branched group with up to 25 carbon atoms, such as methyl, ethyl, propyl, butyl, sec-butyl, tert-butyl, pentyl, hexyl, heptyl, octyl, stearyl, 1-methylpentyl, 5-methylhexyl, trichloromethyl, and trifluoromethyl. Alkylene groups can include such groups as isopropylene, isobutylene, tert-butylene, and vinyl and allyl groups.

The $R_1$, $R_2$ and $R_3$ groups are each independently a substituted or non-substituted alkyl group which can be linear or branched, such as the alkyl groups listed above for $Ak_1$, $Ak_2$, $Ak_3$ and $Ak_4$. The counter anion can be any anion such as $Cl^-$, $Br^-$, $I^-$ and $SbF_6^-$.

In a preferred embodiment of the invention, a strong (two-photon absorption cross section δ>50 GM) two-photon absorbing distyrylbenzene chromophore has the following structural formula (II):

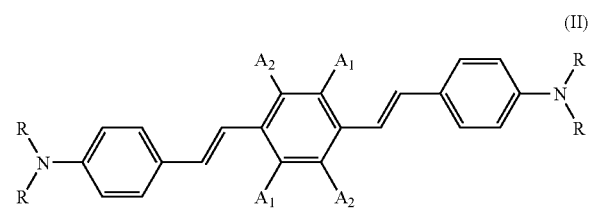

wherein $A_1$ and $A_2$ are each independently a hydrogen, or a donor or acceptor group; and R is $[(CH_2)_n]_6$—$NR'_3X$, where R' is $(CH_2)_m$—H, X is any anion, n is from 1 to 10 and m is from 1 to 10. The chromophore is made water-soluble by the quaternary amine moieties at the para positions of the styryl groups, and has charge-transfer properties via donating groups at each end of the pi-electron system and different functional groups at the center ring. In a particular embodiment, donor and acceptor groups can be on the same center ring of the distyrylbenzene chromophore.

Specific examples of distyrylbenzene chromophores having donor groups on the center ring are (III):

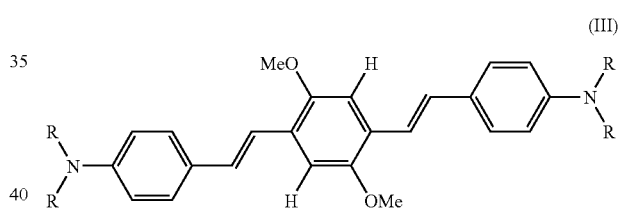

where R is $(CH_2)_6$—$NR'_3X$ and R' is $CH_3$.

Specific examples of distyrylbenzene chromophores having acceptor groups on the center ring are:

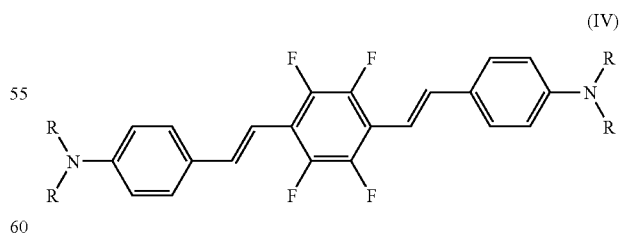

where R is $(CH_2)_6$—$NR'_3X$ and R' is $CH_3$.

The following examples will illustrate the invention. Examples 1–6 show the synthesis and characterization of molecules based on structural formula (II) in which $A_1=A_2=$H, n=2 and m=1.

The following reaction scheme was used:

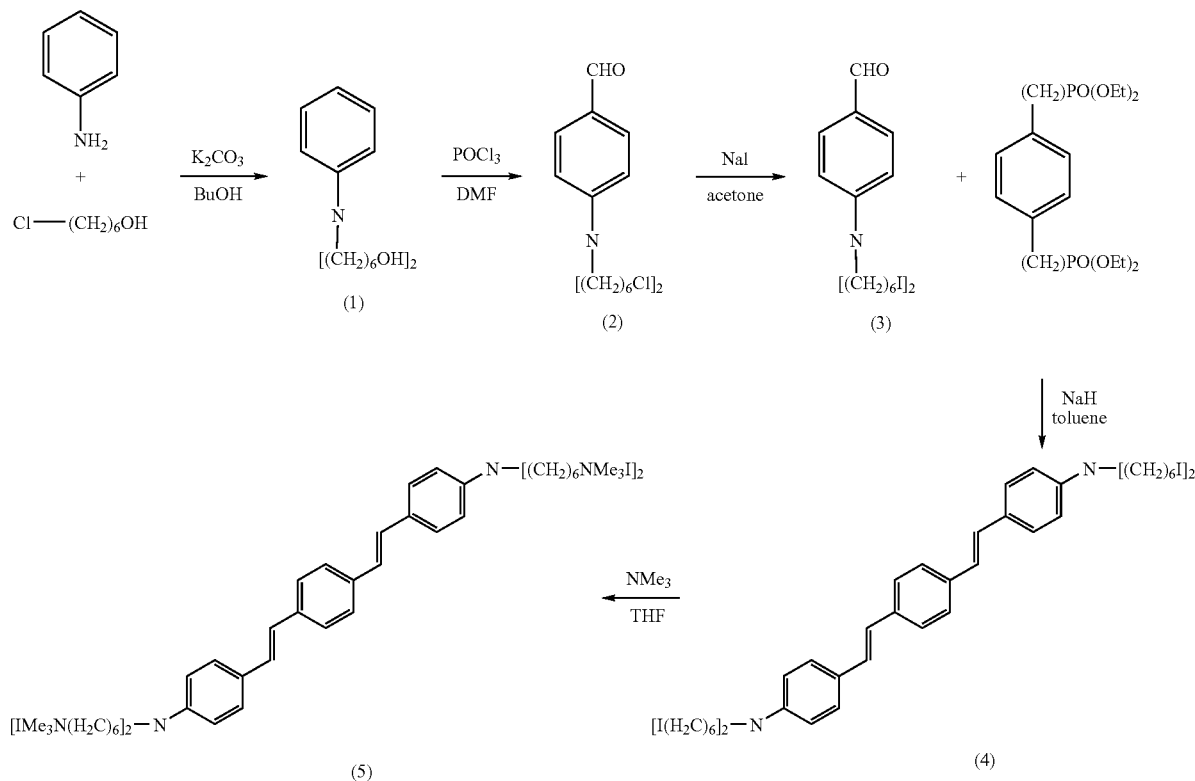

Chemicals were purchased from Aldrich, except 2,5-dimethyltherephthalonitrile, which was purchased from TCI America and used without further purification. $^1$H and $^{13}$C NMR spectra were recorded on a Bruker AMX-400 NMR operating at 400.1 and 100.6 MHz respectively. UV/vis absorption spectra were recorded on a Perkin-Elmer Lambda 19 spectrophotometer and photoluminescence spectra on a Spex Fluorolog 2 spectrometer In the Examples, the number in parenthesis following a compound name refers to the numbered compound in the preceding reaction scheme.

EXAMPLE 1

N,N-Bis-(6-hydroxyhexyl)-aniline (1)

A mixture of 9.3 g (100 mmol) freshly distilled aniline, 30.0 g (220 mmol) 6-chloro-1-hexanol and 30.4 g (220 mmol) potassium carbonate were heated in 50 ml of n-butanol under reflux for 4 days. After cooling the solids were filtered of and the solvent is removed in vacuum. Purification by liquid chromatography (ethyl acetate/hexane 2:1) afforded 17.6 g (60%) of a colorless oil.$^1$ H-NMR (400 MHz, CDCl$_3$): δ=7.18 (m, 2H), 6.61 (m, 3H), 3.91 (t, J=6.4 Hz, 4H), 3.67 (t, J=6.4 Hz, 4H), 1.90–1.77 (m, 4H), 1.70–1.53 (m, 4H), 1.50–1.31 (m, 8H). $^{13}$C-NMR (100 MHz, CDCl$_3$); 148.19, 129.31, 115.33, 111.86, 62.793, 51.06, 32.78, 27.30, 27.05, 25.76. EI-MS: 293 (M+), 206 (M$^+$-C5H10OH), 120 (M$^+$-2 C5H10OH). Calcd for C$_{18}$H$_{31}$NO$_2$: C, 79.67; H, 10.65; N, 4.77; O, 10.90

EXAMPLE 2

N,N-Bis-(6-chlorohexyl)4-amino)-benzaldehyde (2)

10.9 ml (114 mmol, 17.5 g) phosphorus oxychloride was added dropwise to 40 ml of dry DMF at 0 degree. After 15 min 11.1 g (38 mmol) of (1) in 20 ml DMF is added through a dropping funnel within 30 min. The resulting solution was heated to 100 degree for 2 h. After cooling to 40 degree it was poured into 200 g of ice. The pH of the mixture was adjusted to 6.0 by adding potassium acetate. The product was extracted by two portions of 200 ml of methylenechloride each. The organic phase was washed with water and dried over MgSO$_4$. The solvent was evaporated and the crude product was purified by liquid chromatography (chloroform/hexane 3:2). $^1$H-NMR (400 MHz, CDCl$_3$): δ=9.71 (s, 1H), 7.71 (d, J=8.4 Hz, 2H), 6.65 (d, J=8.4 Hz, 2H), 3.55 (t, J=9.4 Hz, 4H), 3.36 (t, J=7.2 Hz, 4H), 1.89–1.81 (m, 4H), 1.64–1.60 (m, 4H), 1.48–1.36 (m, 8H). $^{13}$C-NMR (100 MHz, CDCl$_3$): δ=190.18, 152.66, 132.46, 124.87, 110.90, 51.14, 45.17, 32.73, 27.23, 26.88, 26.51. EI-MS: 357 (M+), 252 (M$^+$-C5H10Cl), 148 (M$^+$-2 C5H10Cl). Calcd for C$_{19}$H$_{29}$Cl$_2$NO: C, 63.68; H, 8.16; Cl, 19.79; N, 3.91; O, 4.46

EXAMPLE 3

N,N-Bis-(6-iodohexyl)-4-amino-benzaldehyde (3)

8.9 g (14.7 mmol) N,N-Bis-(6-chlorohexyl)-4-amino)-benzaldehyde (2) and 37.5 g (250 mmol) Sodium iodide were dissolved in 200 ml dry Acetone and heated under reflux for two days. The solvent was mostly evaporated and the resulting mixture was diluted with 300 ml of dichloromethane and washed three times with an equal amount of water. The organic phase was dried over $MgSO_4$ and the solvent evaporated. Purification of the raw material by liquid chromatography with chloroform/hexane (3:2) afforded 10.7 g of 7 (80%). $^1$H-NMR (400 MHz, $CDCl_3$): δ=9.70 (s, 1H), 7.69 (d, J=8.4 Hz, 2H), 6.63 (d, J=8.4 Hz, 2H), 3.34 (t, J=7.6 Hz, 4H), 3.19 (t, J=6.8 Hz, 4H), 1.86–1.81 (m, 4H), 1.64–1.60 (m, 4H), 1.47–1.33 (m, 8H). $^{13}$C-NMR (100 MHz, $CDCl_3$); 190.07, 152.54, 132.32, 124.73, 110.82, 51.03, 33.38, 30.34, 27.06, 26.04, 7.19. EI-MS: 541 (M+), 344 ($M^+$-C5H10Cl), 148 ($M^+$-2 C5H10I). Calcd for $C_{19}H_{29}I_2NO$: C, 42.16; H, 5.40; I, 46.89; N, 2.59; O, 2.96.

EXAMPLE 4

Precursor Chromophore (4)

378 mg (1.00 mmol) 1,4-dibenzylphosphonate and 1623 mg (3.00 mmol) of the aldehyde (3) were dissolved in dry THF and place in an ice bath. 2.2 mmol of sodium hydride was added. The suspension was stirred for three days at room-temperature. The resulting mixture was diluted by 200 ml of methylenechloride and washed twice with brine. The organic layer was dried over $MgSO_4$, and the solvent was evaporated. The crude material was purified by liquid chromatography (methylene chloride/hexane 2:1), affording 450 mg (39%) of a yellow colored solid. $^1$H-NMR (400 MHz, $CDCl_3$): δ=7.45 (s, 4H), 7.39 (d, J=8.8 Hz, 4H), 7.04 (d, J=15.6 Hz, 2H), 6.89 (d, J=15.6 Hz, 2H), 6.63 (d, J=8.8 Hz, 4H), 3.30 (t, J=7.6 Hz, 8H), 3.22 (t, J=6.4 Hz, 8H), 1.89–1.82 (m, 8H), 1.64–1.57 (m, 8H), 1.49–1.43 (m, 8H), 1.41–1.35 (m, 8H). $^{13}$C-NMR (100 MHz, $CDCl_3$): δ=147.73, 136.87, 128.32, 127.97, 126.41, 125.14, 123.89, 111.97, 51.15, 33.66, 30.59, 27.39, 26.32, 7.41. Calcd for $C_{46}H_{64}I_4N_2$: C, 47.93; H, 5.60; I, 44.04; N, 2.43

EXAMPLE 5

Chromophore (5)

200 mg of the precursor chromophore (4) was dissolved in 3 ml THF and cooled down to −78° C. An excess of trimethylamine was added by condensation. The solution was allowed to warm up to room temperature. After 1 day about 20 ml of water and another portion of trimethylamine was added and the mixture was stirred for one further day. Afterwards all solvents were evaporated. The remaining material was redissolved in water and filtered. Solvents were evaporated and the product was dried in vacuo. $^1$H-NMR (400 MHz, $CDCl_3$): δ=7.48 (s, 4H), 7.39 (d, J=9.2 Hz, 4H), 7.09 (d, J=16.4 Hz, 2H), 6.90 (d, J=16.4 Hz, 2H), 6.64 (d, J=9.2 Hz, 4H), 3.28 (m, 8H), 3.04 (s, 36H) 1.68 (m, 8H), 1.55 (m, 8H), 1.34 (m, 16H) $^3$C-NMR (100 MHz, $CDCl_3$): δ=147.35, 136.22, 127.70, 124.06, 112.75, 111.51, 65.23, 52.16, 49.93, 26.68, 25.96, 25.77, 22.10. Calcd: C, 50.15; H, 7.26; I, 36.54; N, 6.05

EXAMPLE 6

Characterization

FIG. 1 shows the two-photon absorption of molecules for which $A_1=A_2=H$ (solid line) and $A_1=A_2=F$ (dotted line), and where n=1 and m=1, according to formula (II). These measurements were in reference to standard rhodamine B and were performed using two photon fluorescence measurements.

Figure 2:
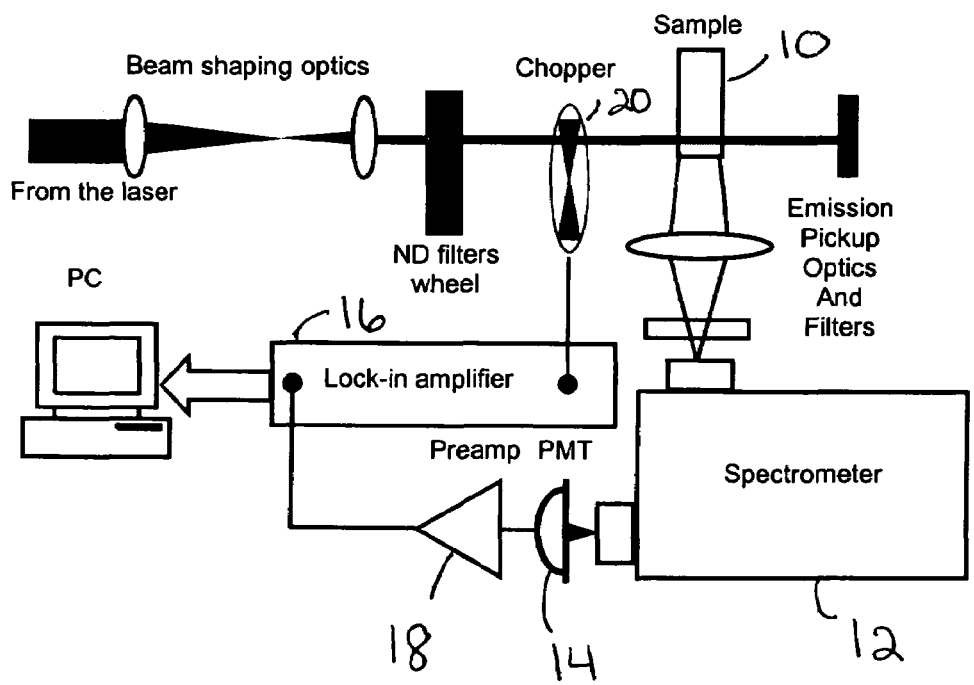
FIG. 2 is a schematic drawing showing a set-up for measuring two-photon absorption photoluminescence spectra.

Two-photon absorption spectra were measured using two-photon absorption photoluminescence (TPA PL) spectroscopy. Two photon fluorescence was excited in samples by directing a tightly collimated, high-intensity laser beam on a sample, as depicted in the schematic drawing of FIG. 2. The emission from the sample 10 was collected at a 90° angle by a high numerical aperture lens and directed to the entrance slit of a spectrometer 12. The radiation dispersed by the spectrometer was detected by a photomultiplier tube 14 connected to a digital lock-in amplifier 16 through a low-noise current preamplifier 18. The lock-in amplifier was synchronized to an optical chopper 20 modulating the pump beam intensity with a frequency of 500 Hz. Excitation pulses with typical duration of 90 fs and energy of ~6 nanoJoules (nJ) were produced by a mode-locked laser (Spectraphysics Tsunami) with repetition rate of 82 MHz. The laser's wavelength could be tuned continuously within the spectral range 690–1000 nm. Neutral density filter wheel has been used to attenuate the energy of the laser pulses down to desirable level.

The spectrally integrated intensity of the two photon fluorescence excited with this configuration can be determined by the following expression:

$$I = A\eta \int_{-\infty}^{\infty} \frac{I_0^2(t)\delta cl}{1 + I_0(t)\delta cl} dt \quad (a)$$

where δ is the two-photon absorption cross-section, c is the concentration of two-photon absorption-active molecules, l is the interaction length, and η is the fluorescence efficiency. Factor A includes all constant parameters specific for a given experimental setup (e.g. geometric factors, spectrometer and detector efficiencies). Function $I_0(t)$ describes the temporal profile of the excitation pulse. With a weak excitation regime, it can be assumed that $I_0(t)\delta nl<<1$. Then expression (a) becomes:

$$I = A\eta\delta cl \int_{-\infty}^{\infty} I_0^2(t) dt = B\eta\delta cl P^2 \quad (b)$$

where P and B are excitation light power and a constant, respectively. Since B is difficult to determine, a relative measurements technique was employed using a reference sample with a known two-photon absorption spectrum. With this relative technique, the ratio of the integrated PL intensities for the reference and studied samples can be expressed as:

$$\frac{I}{I_{ref}} = \frac{\eta\delta c}{\eta_{ref}\delta_{ref}c_{ref}} \frac{P^2}{P_{ref}^2} \quad (c)$$

where the index ref denotes values relative to the reference measurements. It was assumed that all experimental parameters were identical during the whole series of measurements, except the power of the pump radiation P and sample specific parameters η, δ, and c. From (c), one can easily find the two-photon absorption cross-section of the compound studied:

$$\delta = \frac{\eta_{ref}\delta_{ref}c_{ref}}{\eta c} \frac{P_{ref}^2}{P^2} \frac{I_{ref}}{I}. \quad (d)$$

Molar concentrations were determined from optical absorption spectra, using molar absorptivity values supplied by a compound's manufacturer or obtained from volumetric measurements. In all measurements, the concentration of material did not exceed $10^{-4}$ M in order to avoid self-quenching of emission. Fluorescence quantum yields have been verified using a referenceless technique adopted for the liquid phase measurements. Both absorption and emission spectra of samples were monitored during the entire series of measurements. After being properly degassed, the samples did not exhibit any sign of degradation within the scope of the experiment.

As reference materials, we used three laser dyes: Coumarin 503 (purchased from Exciton Inc. as Coumarin 307), fluorescein (purchased from Acros Inc.), and Rhodamine 610 (purchased from Exciton Inc. as Rhodamine B). Coumarin 503 and Rhodamine 610 were dispersed in methanol, and fluorescein was dissolved in water with the addition of NaOH (pH=11). Two-photon absorption spectra in the spectral interval of interest were taken from the literature.

In order to use equation (c), TPA PL studies were performed in a low excitation regime. This was verified by measuring fluorescence intensity pump dependence. In all cases, it was very close to a pure quadratic function. Using a set-up as in FIG. 2, TPA PL spectra were collected at different excitation wavelengths. In all cases, the spectra matched single-photon fluorescence spectra. The recorded spectra were integrated numerically and the resulting values were substituted in formula (c) along with the excitation power. The latter values were measured using a thermopile optical power meter (Newport-815C).

EXAMPLE 7

Figure 3:
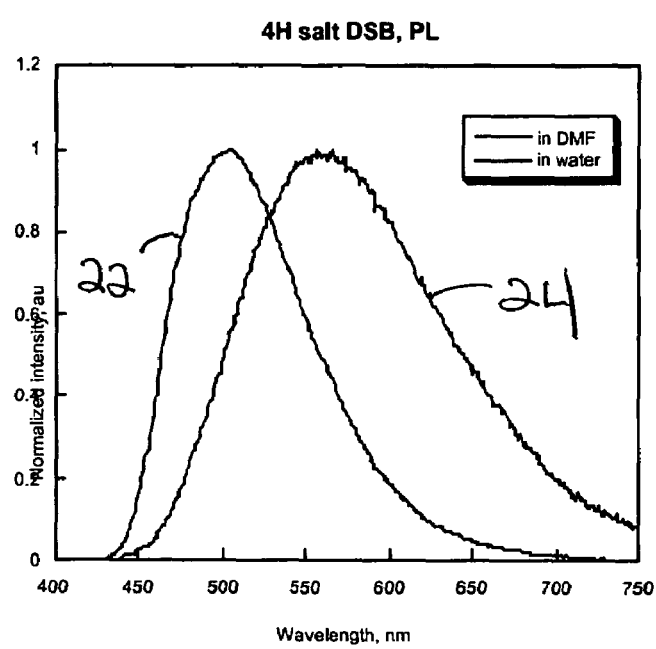
FIG. 3 is a graph showing spectra of the molecule in dimethyl formamide and in $H_2O$.

FIG. 3 shows the photoluminescence spectra of molecules in which $A_1=A_2=H$, n=1 and m=1, according to formula (II). The spectra were taken in dimethyl formamide (DMF) (left curve 22) and $H_2O$ (right curve 24). The shift in PL maxima corresponds to changes in solvent polarity. The chromophore was dissolved in dimethyl formamide or water at a final concentration of about $1 \times 10^{-6}$ M (corresponding to optical density of 0.1). The photoluminescence spectra were recorded on a Spex Fluorolog 2 spectrometer and normalized.

EXAMPLE 8

Chromophores of the present invention can be used in optoelectronics technologies such as optical data storage and 3-D microfabrication. The molecules have a conjugated pi-electron system with donating groups at each end of the pi-electron system, resulting in a large two-photon absorption cross section $\delta$ as described in Example 6. The molecules can have a strong two-photon excited electron donating property, which can be used to initiate polymerization of vinyl or acrylate monomers.

A water-soluble chromophore of the present invention, such as chromophore (5), can be incorporated into a sol-gel matrix containing acrylate monomers. The chromophore and acrylate containing sol-gel matrix can be prepared as a thin film or monolith. When a femt-second laser with an appropriate wavelength is focused at the desired position in the film or monolith, the irradiated small volume, which has a dimension of about $\lambda^3$ (cubic of the irradiate wavelength), undergoes changes in reflectance which is caused by a change in the refractive index. This reflectance change can be used as a recording bit in the optical data storage.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular described embodiments. Compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such compositions of matter, means, methods, or steps.

What is claimed is:

1. A chromophore having the following structural formula (I):

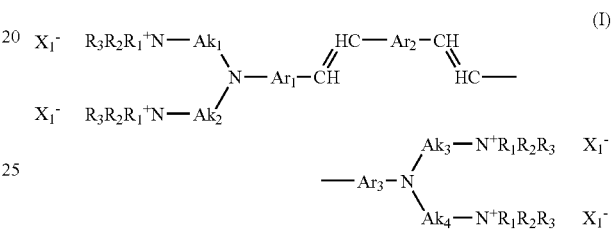

wherein $Ar_1$, $Ar_2$ and $Ar_3$ are each independently a substituted or non-substituted aromatic hydrocarbon or aromatic heterocyclic ring; $Ak_1$, $Ak_2$, $Ak_3$ and $Ak_4$ are each independently a substituted or non-substituted alkyl or alkylene group; $R_1$, $R_2$ and $R_3$ are each independently a substituted or non-substituted alkyl group; and $X_1$ is a counter anion.

2. The chromophore of claim 1 wherein $Ar_1$, $Ar_2$ and $Ar_3$ are single aromatic rings.

3. The chromophore of claim 2 wherein $Ar_1$, $Ar_2$ and $Ar_3$ are benzene rings.

4. The chromophore of claim 1 wherein $Ar_2$ includes a donor or acceptor group.

5. The chromophore of claim 1 wherein $Ak_1$, $Ak_2$, $Ak_3$ and $Ak_4$ are each $(CH_2)_n$, where n is from 1 to 10, and $R_1$, $R_2$ and $R_3$ are each $(CH_2)_m$—H, where m is from 1 to 10.

6. A distyrylbenzene chromophore having the following structural formula (II):

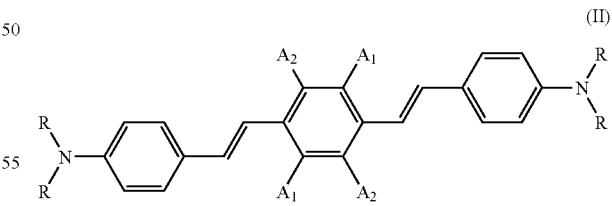

wherein $A_1$ and $A_2$ are each independently a hydrogen, or a donor or acceptor group; and R is $[(CH_2)_n]_6$—$NR'_3X$, where R' is $(CH_2)_m$—H, X is any anion, n is from 1 to 10 and m is from 1 to 10.

7. The chromophore of claim 6 in which the donor group is selected from the group consisting of I, Br, Cl, OC(O)R", SH, OH, SR", OR", NHC(O)R", $NH_2$, NH"R, $S^-$, and $O_-$, where R" refers to an alkyl group containing 1–50 carbon atoms.

8. The chromophore of claim 6 in which the acceptor group is selected from the group consisting of F, C(O)NR''$_2$, C(O)NHR'', C(O)NH$_2$, C(O)OR'', C(O)OH, C(O)R'', C(O)H, CN, S(O$_2$)R'', and NO$_2$, and where R'' refers to an alkyl group containing 1–50 carbon atoms.

9. The chromophore of claim 6 in which A$_1$ and A$_2$ are each hydrogen and n=1.

10. A distyrylbenzene chromophore having the following structural formula (III):

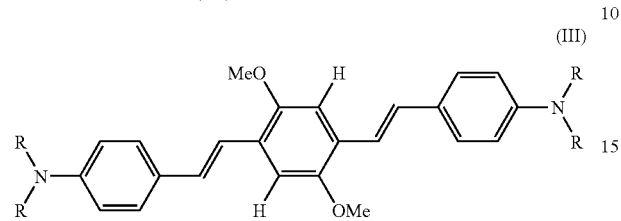

wherein R is (CH$_2$)$_6$—NR'$_3$X, R' is CH$_3$, and X is any anion.

11. A distyrylbenzene chromophore having the following structural formula (IV):

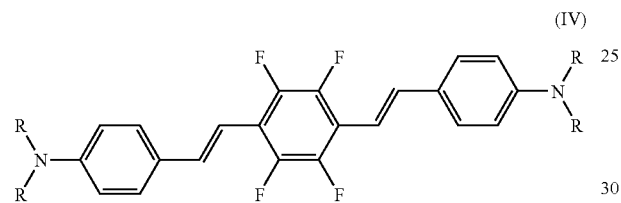

wherein R is (CH$_2$)$_6$—NR'$_3$X, R' is CH$_3$ and X is any anion.

12. A method of preparing a distyrylbenzene chromophore, comprising reacting a 1,4-dibenzylphosphonate with a haloalkylamino-benzaldehyde and adding a trialkylamine by condensation to said distyrylbenzene chromophore whereby to provide water solubility to said chromophore.

13. The method of claim 12 in which said haloalkylamino-benzaldehyde is a N,N-bis-(6-iodoalkyl)-4-amino-benzaldehyde where the alkyl group has from 1 to 10 carbon atoms.

14. The method of claim 13 in which said N,N-bis-(6-iodohexyl)-4-amino-benzaldehyde is prepared by reacting N,N-bis-(6-hydroxyhexyl)-benzaldehyde with phosphorous oxychloride.

15. The method of claim 14 in which said N,N-bis-(6-hydroxyhexyl)-benzaldehyde is prepared by reacting aniline and 6-chloro-1-hexanol with a carbonate.

16. A method of preparing a water-soluble two-photon absorbing distyrylbenzene chromophore, comprising the following steps:

a) reacting analine 6-chloro-1-hexanol and potassium carbonate to yield N,N-Bis-(6-hydroxyhexyl)-aniline of the formula:

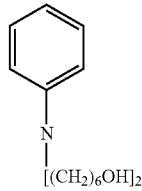

b) reacting N,N-Bis-(6-hydroxyhexyl)-aniline and phosphorous oxychloride to yield N,N-Bis-(6-chlorohexyl)-4-amino)-benzaldehyde of the formula:

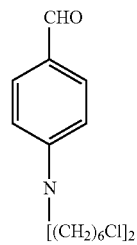

c) reacting N,N-Bis-(6-chlorohexyl)-4-amino)-benzaldehyde and sodium iodide to yield N,N-Bis-(6-iodohexyl)-4-amino-benzaldehyde of the formula:

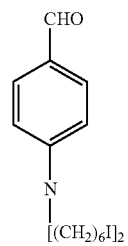

d) reacting N,N-Bis-(6-iodohexyl)-4-amino-benzaldehyde and 1,4-dibenzylphosphonate of the formula

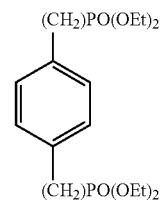

to yield a precursor chromophore of the formula:

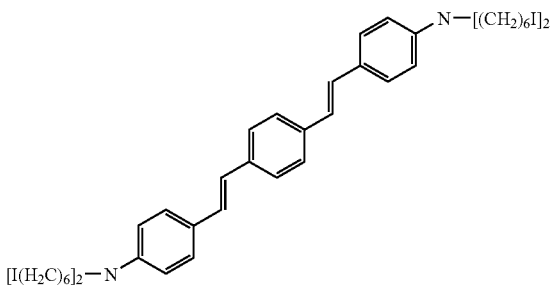

e) reacting the precursor chromophore with trimethylamine to yield a distyrylbenzene chromophore of the formula:

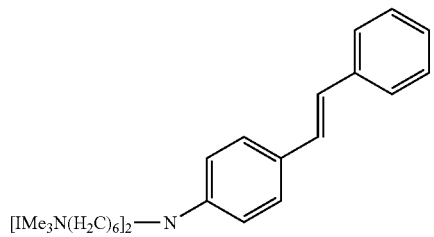
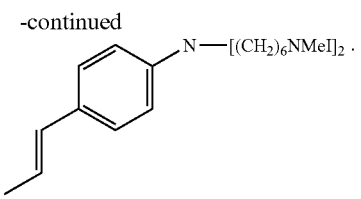
-continued
* * * * *